US008697390B2

(12) United States Patent
Skindersø et al.

(10) Patent No.: US 8,697,390 B2
(45) Date of Patent: Apr. 15, 2014

(54) METHOD AND KIT FOR EXAMINATION OF CELLS USING N-(9-ACRIDINYL) MALEIMIDE (NAM) OR USING 7-DIETHYLAMINO-3-((4'-IODACETYL) AMINO)PHENYL)-4-METHYLKCOUMARIN (CPI)

(75) Inventors: Mette Elena Skindersø, Virum (DK); Helle Frobøse Sørensen, Copenhagen V (DK); Søren Kjaerulff, Hillerod (DK)

(73) Assignee: ChemoMetec A/S, Allerød (DK)

( * ) Notice: Subject to any disclaimer, the term of this patent is extended or adjusted under 35 U.S.C. 154(b) by 0 days.

(21) Appl. No.: 13/003,982

(22) PCT Filed: Jul. 14, 2009

(86) PCT No.: PCT/DK2009/050174
§ 371 (c)(1),
(2), (4) Date: Sep. 8, 2011

(87) PCT Pub. No.: WO2010/006616
PCT Pub. Date: Jan. 21, 2010

(65) Prior Publication Data
US 2011/0312013 A1  Dec. 22, 2011

(30) Foreign Application Priority Data

Jul. 14, 2008  (DK) ................................. 2008 00987
Jul. 14, 2008  (DK) ................................. 2008 00988

(51) Int. Cl.
*C12Q 1/02* (2006.01)
(52) U.S. Cl.
USPC .............................. 435/29; 549/283; 549/275
(58) Field of Classification Search
None
See application file for complete search history.

(56) References Cited

U.S. PATENT DOCUMENTS

| 5,828,716 A | 10/1998 | Bisconte de Saint Julien |
| 2004/0248107 A1 | 12/2004 | Sokolova et al. |

FOREIGN PATENT DOCUMENTS

| EP | 0 601 606 | 6/1994 |
| WO | WO 98/37226 | 8/1998 |
| WO | WO 98/50777 | 11/1998 |
| WO | WO 0028297 | 5/2000 |
| WO | WO 01/77648 | 10/2001 |
| WO | WO 2008/157003 | 12/2008 |

OTHER PUBLICATIONS

Marchetti et al. "Comparison of four fluorochromes for the detection of the inner mitochondrial membrane potential in human spermatozoa and their correlation with sperm motility." (2004) Human Reproduction, vol. 19: 2267-2276.*
Katerinopoulos, "The Coumarin Moiety as Chromophore of Fluorescent Ion Indicators in Biological Systems." (2004) Current Pharmaceutical Design, vol. 10: 3835-3852.*
Grayeski and DeVasto, "Coumarin Derivatizing Agents for Carboxylic Acid Detection Using Peroxyoxalate Chemiluminescence with Liquid Chromotography" (1987) Analytical Chemistry, vol. 59: 1203-1206.*
Breeuwer and Abee, "Assessment of viability of microorganisms employing fluorescence techniques" (2000) International Journal of Food Microbiology vol. 55: 193-200.*
Petersen and Dailey, "Diverse Microglial Motilty Behaviors During Clearance of Dead Cells in Hippocapal Slices" (2004) Glia vol. 46: 195-206.*
Akasaka et al., 1990, "Fluorometric determination of sulfite in wine by N-(9-acridinyl)maleimide", Agric. Biol. Chem., 54, 2, pp. 501-504.
Baranowska-Kortylewicz et al., 1993, "Labeling of sulfhydryl groups in intact mammalian cells with coumarins", ioconjugate Chemistry, vol. 4, No. 4, pp. 305-307.
Durand et al., 1983, "Flow cytometry techniques for studying cellular thiols", Radiation Research, 95, pp. 456-470.
Evenson et al., 1989, "Flow cytometric analysis of rodent epididymal spermatozoal chromatin condensation and loss of free sulfhydryl groups", Molecular Reproduction and Development, vol. 1, No. 4, pp. 283-288.
Fu et al, 2005, "Spectrofluorimetric determination of thiols in biological samples with a new fluorescent probe 3-maleimidylbenzanthrone", Analytical Letters, 38, pp. 791-802.
Hansen et al., 1996, "Inactivation of MET10 in brewer's yeast specifically increases SO2 formation during beer production", Nature Biotech, 14, pp. 1587-1591.
Kamata et al., 1993, "A sensitive fluorometric assay of glutathione reductase activity with N-(9-acridinyl)maleimide", Analytical Sciences, vol. 9, No. 6, pp. 867-870.
Kanda et al., 1998, "Histone-GFP fusion protein enables sensitive analysis of chromosome dynamics in living mammalian cells", Curr Biology, 8, pp. 377-385.

(Continued)

*Primary Examiner* — Jon P Weber
*Assistant Examiner* — Teresa E Knight
(74) *Attorney, Agent, or Firm* — Gifford, Krass, Sprinkle, Anderson & Citkowski, P.C.

(57) ABSTRACT

The present invention provides simple, rapid methods and procedures for analyzing cells, hereunder quantitative and qualitative assessment of cells. The present invention relates to the use of N-(9-acridinyl)maleimide (NAM) or to the use of 7-diethylamino-3-((4'-(iodoacetyl)amino)phenyl)-4-methylcoumarin (CPI), particularly detectable upon its reaction with species (e.g., sulphur-containing species) present in higher concentrations in intact (e.g., living) cells than in non-intact (e.g., dead) cells. The present invention also relates to the use of NAM or to the use of 7-diethylamino-3-((4'-(iodoacetyl)amino)phenyl)-4-methylcoumarin (CPI), particularly detectable upon its reaction with species present in intact and/or non-intact cells. Moreover, the present invention relates to the use of measuring techniques and/or instruments coupled with the use of NAM or with the use of 7-diethylamino-3-((4'-(iodoacetyl)amino)phenyl)-4-methylcoumarin (CPI). The invention further relates to compositions used in methods for analyzing cells.

18 Claims, 11 Drawing Sheets

(56) References Cited

OTHER PUBLICATIONS

Kobayashi et al, 1994, "Possible role of metallothionein in the cellular defense mechanism against UVB irradiation in neonatal human skin fibroblasts", Photochemistry and Photobiology, vol. 59, No. 6, pp. 650-656.

Lutz et al., 1999, An advanced culture method for generating large quantities of highly pure dendritic cells from mouse bone marrow. J Immunol Methods 223, pp. 77-92.

Moreno et al., 1991, "Molecular genetic analysis of fission yeast *Schizosaccharomyces pompe*", Methods Enzym, 194, pp. 795-823.

Odom et al., 1990, "Movement of tRNA but not the nascent peptide during peptide bond formation on ribosomes", Biochemistry, vol. 29, No. 48, pp. 10734-10744.

Olive et al, 1982, "Characterization of the uptake and toxicity of a fluorescent thiol reagent", Cytometry, Alan Liss, New York, US, vol. 3, No. 5, pp. 349-353.

Poot et al., 1991, "Flow cytometric analysis of cell cycle-dependent changes in cell thiol level by combining a new laser dye with hoechst 33342", Cytometry, Alan Liss, New York, US, vol. 12, No. 2, pp. 184-187.

Rice et al., 1986, "Quantitative analysis of cellular glutathione by flow cytometry utilizing monochlorobimane: Some applications to radiation and drug resistance in vitro and in vivo", Cancer Research, 46, pp. 6105-6110.

Seibel et al., 2007, "Nuclear localization of enhanced green fluorescent protein homomultimers", Anal Biochem, 368, pp. 95-99.

Sippel, 1981, "New fluorochromes for thiols: maleimide and iodoacetamide derivatives of a 3-phenylcoumarin fluorophore". J Histochem Cytochem., 29(2), pp. 314-316.

Styrkarsdottir et al., 1993, "The smt-0 mutation which abolishes mating-type switching in fission yeast is a deletion", Curr Genet, 23, pp. 184-186.

Yokoi et al., 1984, "Immuno cytochemical detection of desmin in fat storing cells ito cells", Hepatology, vol. 4, No. 4, pp. 709-714.

Østergaard et al., 2004, "Monitoring disulfide bond formation in the eukaryotic cytosol", J Cell Biol, vol. 166, 3, pp. 337-345.

\* cited by examiner

Phase contrast

NAM

PI

METHOD AND KIT FOR EXAMINATION OF CELLS USING N-(9-ACRIDINYL) MALEIMIDE (NAM) OR USING 7-DIETHYLAMINO-3-((4'-IODACETYL) AMINO)PHENYL)-4-METHYLKCOUMARIN (CPI)

CROSS-REFERENCE TO RELATED APPLICATIONS

This application is the U.S. national phase of PCT/DK2009/050174 filed Jul. 13, 2009, which claims priority of Danish Patent Application Nos. PA 2008 00987 and PA 2008 00988 filed Jul. 14, 2008.

All patent and non-patent references cited in the application, or in the present application, are also hereby incorporated by reference in their entirety.

FIELD OF INVENTION

The present invention provides simple, rapid methods and procedures for analyzing cells, hereunder quantitative and qualitative assessment of cells. The present invention relates to the use of N-(9-acridinyl)maleimide (NAM) particularly detectable upon its reaction with species (e.g., sulphur-containing species) present in higher concentrations in intact (e.g., living) cells than in non-intact (e.g., dead) cells. The present invention also relates to the use of NAM particularly detectable upon its reaction with species present in intact and/or non-intact cells. Moreover, the present invention relates to the use of measuring techniques and/or instruments coupled with the use of NAM. The invention further relates to compositions used in methods for analyzing cells.

Furthermore, the present invention provides simple, rapid methods and procedures for analyzing cells, hereunder quantitative and qualitative assessment of cells. The present invention relates to the use of 7-diethylamino-3-((4'-(iodoacetyl)amino)phenyl)-4-methylcoumarin (CPI) particularly detectable upon its reaction with species (e.g., sulphur-containing species) present in higher concentrations in intact (e.g., living) cells than in non-intact (e.g., dead) cells. The present invention also relates to the use of CPI particularly detectable upon its reaction with species present in intact and/or non-intact cells. Moreover, the present invention relates to the use of measuring techniques and/or instruments coupled with the use of CPI. The invention further relates to compositions used in methods for analyzing cells.

BACKGROUND OF INVENTION

Characterizing cell viability and other cell features can provide useful information with respect to a wide range of applications. However, methods presently employed are quite complex and time consuming. Existing methods make use of permeable fluorophores with an attached ester linker that is subsequently cleaved when present in cells and thereafter emits fluorescens. This technique has however drawbacks including extended incubation times (several minutes). Rhodamin is used to determine the present state of cell viability but do no cross the permeable cell membrane.

SUMMARY OF INVENTION

The present invention provides a general strategy for rapid analysis of viable cells. The invention relates to methods including labelling agents that are freely taken up by cells and capable of reacting with intracellular thiols (e.g., —SH in cysteine-containing peptides such as glutathione). Since the labelling agents essentially react momentanously with intracellular thiols no incubation time is required for measurement of viability. It has been found that only viable intact cells comprises thiols in so high amounts that it is possible to detect the cells using a labelling agent reacting with the thiols, as opposed to dead cells that comprises no or so little amount of thiols that they are not detectable using the labelling agents according to the invention. In particular the labelling agents comprises a label that is activated, ie. visible in the system used, only after the reaction with the thiols have taken place. Thereby only the cells comprising thiols are made visible in the system used.

In one aspect the methods according to the invention in general involve the use of N-(9-acridinyl)maleimide (NAM) (cf. 1)

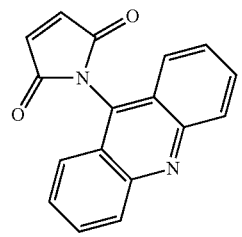

wherein the C2=C3 double bond in the maleimide group is a group that is reactive in the presence of a specific analyte (or species), and upon such reaction to give NAM optical and/or spectral properties different from those of NAM alone. After the substrate enters the cells, the C2=C3 double bond in the maleimide group in NAM reacts with the intracellular analyte (or species) to make NAM detectable by the change in optical and/or spectral properties.

In another aspect the methods according to the invention in general involve the use of 7-diethylamino-3-((4'-(iodoacetyl)amino)phenyl)-4-methylcoumarin (CPI). CPI readily react with all thiols including those found in proteins and peptides such as glutathione (GSH). During the reaction the halide is displaced and a thioether is formed. (Reaction scheme 1)

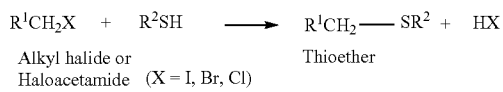

Accordingly, in one aspect the invention relates to a method for quantitative and/or qualitative assessment of cells in a sample, said method comprising
  providing a sample
  adding a labelling agent to said sample, wherein said labelling agent comprises N-(9-acridinyl)maleimide (NAM), or comprises 7-diethylamino-3-((4'-(iodoacetyl)amino)phenyl)-4-methylcoumarin (CPI),
  reacting said labelling agent with said sample obtaining a labelled biological sample,
  quantitatively and/or qualitatively assessing the cells in the labelled sample.

It has further been found that thiols (e.g., cysteine —SH groups in glutathione or other peptides or proteins) could be oxidized to disulphides by oxygen present in cells. In living (intact) cells the enzyme machinery could be capable of reducing disulphides back to thiols. In dead (non-intact) cells, however, the enzyme machinery indicates that this is not working and as a result thiol concentrations are much lower than in living cells.

It has been found that with NAM or CPI as a fluorogen introduced into a cell, its latent fluorescence might only—or at least to a greater extent—be realized in a living cell due to the higher concentration of thiols than in dead cells. Further, a fine-tuning of the reactivity of the maleimide group towards different types of thiols (e.g., various more or less sterically hindered thiols and/or aromatic —SH versus alkyl —SH and/or —SH bound to more or less electron-donating and/or electron-withdrawing groups) may be obtained, for example using NAM where the C2=C3 double bond of the maleimide group are substituted (c.f., e.g., 2 in which either one or both of R1 and R2 optionally can be more or less

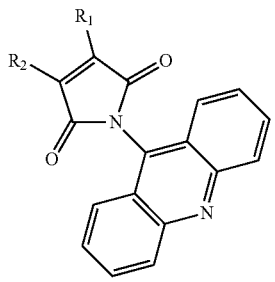

2

In another aspect the invention relates to a kit for quantitative or qualitative assessment of viable cells comprising a labelling agent as defined above and instructions for reacting said labelling agent with a biological sample.

Furthermore, the invention relates to a method for quantitative or qualitative assessment of cells in a sample,
  providing a sample comprising the cells to a sample domain,
  adding a labelling agent to said biological sample, wherein said labelling agent comprises N-(9-acridinyl)maleimide (NAM), or wherein said labelling agent comprises 7-diethylamino-3-((4'-(iodoacetyl)amino)phenyl)-4-methylcoumarin (CPI), and reacting said labelling agent with said biological sample obtaining a labelled sample,
  exposing, onto an array of active detection elements, an at least one-dimensional spatial representation of electromagnetic signals having passed from the domain, the representation being one which is detectable as an intensity by individual active detection elements, under conditions which will permit processing of the intensities detected by the array of detection elements during the exposure in such a manner that representations of electromagnetic signals from the biological particles are identified as distinct from representations of electromagnetic signals from background signals, and preferably wherein the spatial image exposed onto the array of active detection elements is subject to such a linear enlargement that the ratio of the image of a linear dimension on the array of detection elements to the original linear dimension in the exposing domain is smaller than 20:1,
  processing the intensities detected by the detection elements in such a manner that signals from the biological cells are identified as distinct from background signals, and based on the results of the processing obtaining a quantitative or qualitative assessment of the cells.

Lastly, the present invention relates to a composition for assessing samples comprising cells, wherein said composition comprises N-(9-acridinyl)maleimide (NAM), or wherein said composition comprises 7-diethylamino-3-((4'-(iodoacetyl)amino)phenyl)-4-methylcoumarin (CPI).

DETAILED DESCRIPTION OF THE INVENTION

Figure 1:
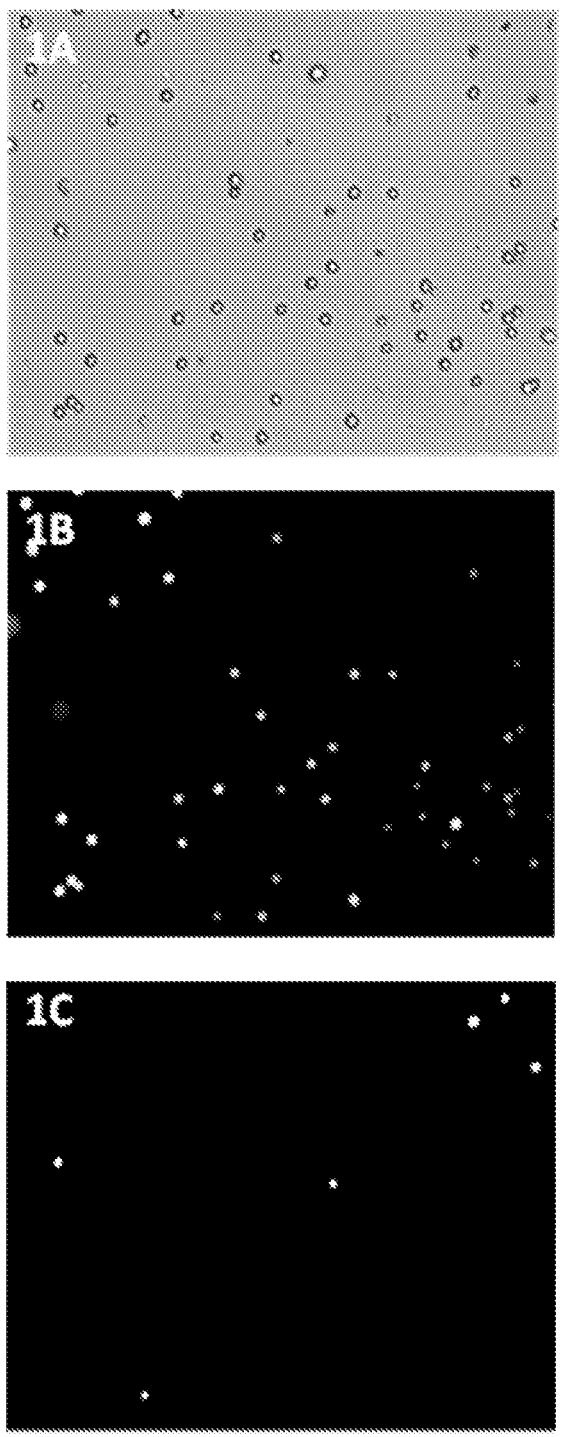
FIG. 1 shows phase contrast images and images from two filters of Jurkat cells that are stained with NAM and PI and discriminates between live and dead cells.

The present invention relates to the use of N-(9-acridinyl)maleimide (NAM) or the use of 7-diethylamino-3-((4'-(iodoacetyl)amino)phenyl)-4-methylcoumarin (CPI) for assessing cells, in particularly viable cells as well as for distinguishing living cells from dead cells, as well as providing detailed information about the cells, such as apoptosis and stress/health status. Accordingly, in one embodiment determination of cell viability includes metabolic activity, metabolite quantification, cell division, proliferation, health, stress level, apoptosis, necrosis or other state of condition.

Furthermore, in one embodiment the invention relates to determination of cell viability, in particularly includes determination of mobility and/or quantification of viable cells.

The term cell viability is used in its normal meaning, ie. a determination of living or dead cells, based on a total cell sample. A number of analysis of the viable cells may be performed, such as quantification of the viable cells, determination of mobility of the cells, or for example determination of morphology of viable cells, localisation of viable cells etc. For example cell viability counts have a tremendous number of applications. Cell viability measurements may be used to evaluate the death or life of a specific cell type, such as for example cancerous cells, in other applications cell viability tests might calculate the effectiveness of a pesticide or insecticide, or evaluate environmental damage due to toxins, see also below with respect to examples of samples.

Testing for cell viability usually involves looking at a sample cell population and staining the cells to show which are living and which are dead.

It has been found that the labelling agent according to the invention is particularly effective in staining living cells only thereby offering the opportunity of distinguishing living cells from dead cells in a sample. A great advantage of the present invention is the fast result obtained.

The term cell mobility generally refers movements of the cell, such as cell motility as well as cell differentiation and cell proliferation, wherein motility generally refers to the ability of some cells to move spontaneously and actively, such as sperm cells, propelled by the regular beat of their flagellum, or the bacterium *E. coli*, which swims by rotating a helical prokaryotic flagellum.

As shown in the Examples the labelling agent is present in the nucleus as well as the cytosol of the cell.

Samples

The sample may be any sample, such as a biological sample, comprising cells for which viability should be determined. The method according to the invention applies to analysis of any type of cell or biological material or tissue, including the raw materials and processes associated with the manufacture, storage and transportation of said products, for the presence of viruses, bacteria, fungi, protozoa or components of these organisms.

In particular a biological sample may be selected from a body fluid sample, a tissue sample, a fermentation sample, a liquid cultivation sample, a cell culture sample, a water sample, such as mammalian and yeast cell cultures, a beverage sample, a pharmaceutical sample, a microelectronic product, and cells suspended in a liquid. More particular the biological sample is selected from a blood sample, a urine sample, a saliva sample, a semen sample, a solubilised tissue sample, a milk sample, or selected from a liver sample, a kidney sample, a muscle sample, a brain sample, a lung sample.

The biological sample may be selected from any species, such as a human sample, a mouse sample, a rat sample, a monkey sample, a dog sample Furthermore, the sample may be selected from a culture of cells, such as a bacterial culture, a mammalian cell culture, a protozoa culture or other cell cultures.

The biological material can be taken from raw material and processes associated with the manufacture, storage and transportation of said biological material.

NAM

The invention is further directed to a composition comprising a NAM molecule, said NAM molecule having the following formula (3):

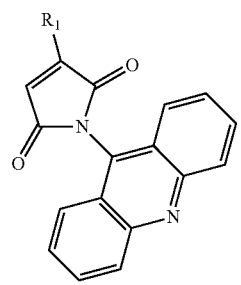

3 wherein: R is $R_a$ or $OR_a$ and $R_a$ is H, $C_1$-$C_8$ alkyl, $CH_2CO_2H$, $CH_2CH_2OH$ or CN.

The labelling agent according to the invention comprises a compound capable of reacting with one or several thiol groups within the cells. NAM may be substituted with substituents and thereby increasing or reducing their water solubility and/or ability to be taken up by the sample.

In a preferred embodiment N-(9-acridinyl)maleimide is present in low concentration in aqueous solution containing small amounts of dimethyl sulfoxide (DMSO). The results from initial experiments demonstrate the markedly superior fluorescence from living cells exposed to NAM as compared with dead cells exposed to NAM.

Application of NAM as a cell viability marker is described in Examples 1, 2 and 3, which show how viability of mammalian and insect cells can be determined using the invention. Using NAM together with the impermeable stain propidium iodide (PI) it was shown that NAM solely stains PI negative cells. As only non-viable cells are permeable to PI, this observation implies that NAM is a viable cell stain.

In Example 4 it is demonstrated that the fluorescent properties of NAM changes in the presence of the —SH reagents reduced glutathione (GSH) and dithiothreitol (DTT), but not by oxidized glutathione (GSSG), suggesting that reacts with the thiol in GSH and DTT forming a fluorescent compound.

Using GFP as reporter it is demonstrated in Example 5 that (reduced) fluorescent NAM (N-(9-acridinyl), maleimide) localizes to the cytosol and nucleus in mammalian cell lines. Hence, NAM is not a DNA specific stain and can be used for whole cell staining. Using propidium iodide as a reporter it is demonstrated in Examples 5 and 6 that NAM can be used to stain living and dead yeast cells. This result implies that NAM, in addition to reduced peptide thiols, reacts with alternative cellular components in yeast cells, such as $SO_3^{-2}$. Hence, NAM can be used for monitoring intracellular metabolites.

CPI

The invention is further directed to a composition comprising a 7-diethylamino-3-((4'-(iodoacetyl)amino)phenyl)-4-methylcoumarin (CPI) molecule

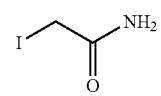

in particularly for use in a labelling agent in cell assays.

The labelling agent according to the invention comprises a compound capable of reacting with one or several thiol groups within the cells. CPI may be substituted with substituents and thereby increasing or reducing their water solubility and/or ability to be taken up by the sample.

In a preferred embodiment CPI is present in low concentration in aqueous solution containing small amounts of dimethyl sulfoxide (DMSO). The results from initial experiments demonstrate the markedly superior fluorescence from living cells exposed to CPI as compared with dead cells exposed to CPI.

Application of CPI as a cell viability marker is described in Example 9, which show how viability of Jurkat cells can be determined using the invention. Using CPI together with the impermeable stain propidium iodide (PI) it was shown that CPI solely stains PI negative cells. As only non-viable cells are permeable to PI, this observation implies that CPI is a viable cell stain.

Double Labelling

In one embodiment the determination of viability includes the labelling agent as discussed above capable of visualising viable cell as well as a labelling agent capable of exclusively labelling dead cells. Thereby the determination may be improved by applying one coloured label to living cells and another coloured label to dead cells improving the visibility of living cells as compared to dead cells. Thus, in one embodiment the cell viability can be determined from quantification of live and dead cells using propidium iodide (PI) to label dead cells and one of the labelling agents discussed above for labelling living cells, and thereby distinguish dead cell from live cells.

While a number of preferred embodiments have been described above, the present invention can be performed and exploited in a large number of ways. In the following, a discussion of a number of measures and details relevant to the invention is given, comprising both preferred embodiments and embodiments which illustrate possibilities of working the invention. Some of the embodiments are given as numbered items, to be understood as brief indications of possible and preferred embodiments in the light of the remaining claims and description herein.

System

The method according to the invention for determining viability of cells in a biological sample may be conducted in any suitable system and apparatus. Accordingly, the method according to the invention may be automated and tailored for monitoring in a microscope, in flow cytometry measurements, in cell counting devices such as instruments from ChemoMetec A/S, studied by cytochemistry etc. In particular the system and apparatus may be as described in PCT/DK98/00175, WO2000/28297, PCT/DK01/00265 or EP96401234.8.

In a preferred embodiment the determination is conducted in a system comprising a sample domain wherein the sample is arranged and detecting the signals from the viable cells.

Sample Domain.

The sample domain established according to the present invention may be a compartment or an equivalent thereof, wherein the sample is located during recording, such as a three-dimensional sample domain. The sample domain may be a part of a flow-through system, wherein each sample is part of a series of samples, whereby one sample is replacing the previous sample in the sample domain. In such embodiments, the sample compartment has both an inlet and an outlet. In other embodiments, the sample compartment only has an inlet.

In one particular embodiment the sample domain is part of a cassette, such as a disposable cassette as described in PCT/DK99/00605. In some embodiments, such a cassette contains pre-added chemicals that contribute to generation of the signal. The sample is contained in the interior of the sample compartment, which normally has an average thickness of between 20 µm and 200 µm, usually between 30 µm and 150 µm and in many practical embodiments between 50 µm and 100 µm.

The part of the sample domain allowing signals to be detected is referred to as the exposing window that can be as little as 1 mm$^2$ or more, preferably with an area of 2 mm$^2$ or more, preferably with an area of 4 mm$^2$ or more, preferably with an area of 10 mm$^2$ or more, preferably with an area of 20 mm$^2$ or more, preferably with an area of 40 mm$^2$ or more, more preferably with an area of 100 mm$^2$ or more.

Sample Volume.

The optimal volume of the sample needed is highly dependent on the number of cells present in the sample and the predetermined statistical quality parameter sought.

Sample volumes may be from 0.005 µl up to several hundred milliliters.

Thus, in one embodiment the sample volumes are from 0.01 to 20 µl, but often a volume of more than 0.1 µl, more than 1.0 µl or even more than 10 µl is used. In another embodiment the sample volume is from 0.02 to 1 ml.

However, in other preferred embodiments of the present invention make it possible to assess cells from a considerably large volume of sample. This can allow the measurement of samples with only few cells of interest per volume of sample. Sample volumes larger than 1 ml and even larger than 100 ml can be used for the analysis, the volume being defined as the total volume of any liquid sample introduced into a sample domain, preferably to any flow system connected to the device, before the measurement of the sample.

Often the design of the sample compartment or the sample is such that the size of the volume of the liquid sample is sufficiently large to permit the assessment of the at least one quantity parameter or the at least one quality parameter to fulfil a predetermined requirement to the statistical quality of the assessment based on substantially one exposure, so that the image is recorded in one exposure.

In another embodiment the assessment of at least one quality parameter or at least one quantity parameter is obtained on the basis of more than one image, preferably two images, more preferably more than two images, more preferably more than four images. In these situations the images are recorded through two, three or more exposures. This can for instance be done to fulfil a predetermined requirement to the statistical quality.

Also, information about the changes in the image in course of time, such as in case of study of mobility, is used in the assessment of at least one quality parameter or at least one quantity parameter, and in such situations more than one exposure may be made.

A large volume of the sample is preferably measured by passing the volume of sample through a cell retaining means, such as a filter, electrical field, magnetic field, gravitational field, such means preferably being included in the device or can be arranged to interact with any sample within the device. The cell retaining means should preferably be able to retain substantially all cells present in a sample, or at least a substantially representative fraction of at least one type of cell present in the sample.

When the cells from a large sample are retained, those cells can be re-suspended in a volume which is less than the volume of sample passed through the cell retaining means.

In one embodiment more than one portion of the same sample material can be subjected to analysis by exposure to the detection system. This can be done by allowing the sample compartment to be moved, thus exposing a different portion of the sample compartment.

Fluorescence

In a preferred embodiment the labelling agent comprises a group capable of emitting fluorescent light. A system based on fluorescence is generally more sensitive than a chromogenic since fewer product molecules are necessary for providing enough electromagnetic radiation to visualise the cells.

A fluorescent label is preferably capable of emitting signals in the wavelength range of from 300 to 1200 nm when excited by excitation light, such as a wavelength between 300 nm to 800 nm, or between 300 nm to 400 nm, or between 400 nm to 500 nm, or between 500 nm to 600 nm, or between 600 nm to 700 nm, or between 700 nm to 800 nm. One preferred fluorescence method is the method of polarised fluorescence.

Excitation Light Source

Often light using any wavelength range, in particular any wavelength between 200 nm to 1700 nm is used for excitation of the labelling agent. In many embodiments of this invention the signals which are detected are attenuation of electromagnetic radiation, for instance caused by absorption or scattering, and in many preferred embodiments of this invention the signals which are detected are emitted from the cells or the samples, for instance emission of photoluminescence (e.g. fluorescence and/or phosphorescence) or Raman scatter, and in other embodiments of this invention the signals which are detected are caused by scatter. In many preferred embodiments of this invention electromagnetic radiation, such as UV or visible light is transmitted onto the sample, in order to give rise to photoluminescence.

The wavelength of the excitation light is selected in accordance with the fluorescent group of the labelling agent. In one embodiment the excitation light emits light having a wavelength between 200 nm to 800 nm, such as between 200 nm to 700 nm, such as between 200 nm to 300 nm, or between 300 nm to 400 nm, or between 400 nm to 500 nm, or between 500 nm to 600 nm, or between 600 nm to 700 nm.

The excitation light source is any suitable light source, such as a light emitting diode (LED), a gas laser, a solid state laser, a laser diode, a gas lamp, such as a xenon lamp, a thermal lamp, such as a halogen lamp, capable of emitting excitation light in the desired range, see above.

It is preferred to use a diverging excitation light, such as light emitting diodes for in a cost-effective manner to expose as large area as possible of the sample to the excitation light.

It may be preferred to use more than one light source for the purpose of increasing the flux of light onto the sample, for instance by using two or more light emitting diodes. It is also possible to use more than one light source where some of the light sources have different electromagnetic properties.

By the use of several LEDs the sample may be exposed to excitation light from several angles leading to a substantially optimal excitation of the sample, the light sources are preferably operated in such a way that all transmit substantially simultaneously.

However for some applications wherein at least a first and a second light source are arranged in the first excitation light means, the first light source having a different wavelength band than the second light source, the light sources may transmit in an alternating manner. By the use of two different light sources it is possible to obtain two different fluorescence signals from the sample. There is no upper limit to the number of LEDs used, but often as many as 30 LEDs are provided, such as up to 50 LEDs, for example up to 100 LEDs, such as up to 150 LEDs, for example up to 200 LEDs, such as 300 or more LEDs.

If a less diverging light source is used a diverging optical means may be arranged in the excitation light path to diverge the excitation light properly.

When using laser diodes as the excitation light the proper divergence may be accomplished by an arrangement of at least 4 laser diodes optionally provided with diverging means.

The incident angle of the excitation light is preferably in the range between 0° and 90°, to the optical axis of the detection system, more preferably between 0° and 60°, such as between 10° and 45° to provide a suitable excitation of the sample.

Magnification.

It has surprisingly been found that it is possible to detect the signals from the labelled cells, even at a rather small magnification such as a magnification less than ×20. At this magnification it has been found that it is possible to quantitatively or qualitatively assess the cells, such as wherein the assessment of cells includes determination of cell viability, such as includes determination of mobility, spatial orientation or morphology, or wherein the assessment of cells includes quantification of viable cells, and/or wherein the assessment of cells includes metabolic activity, metabolite quantification, cell division, proliferation, health, stress level, apoptosis, necrosis or other state of condition.

In some embodiments the invention is preferably carried out at a low magnification whereby it is possible to detect spots in a large volume in one or a few exposures. The magnification factor is preferably below 10, such as below 5, such as 4, more preferably below 4, such as 2, more preferably below 2, such as 1. The advantage of such low magnification are several, among other things increased area of observation and increased depth of focusing implying increased volume exposed to the detection device.

When the spots in question have dimensions which are comparable to the size of a detection element, it is often preferred to have magnification of about 1/1, thus focusing the image of any spot on any one or just few detection elements. This can under some conditions give favourable detection of any signal.

When analysing spots which have dimensions which are comparable to, or bigger than the detection elements used, it is often advantageous to reduce the size of the image of such spot, to a degree where the size of the image is comparable to the size of a detection element. Thus in one embodiment it is preferred that the magnification factor below 1, preferably below 0.9, such as 0.8, more preferably below 0.8 such as 0.6, more preferably below 0.6 such as 0.5.

In these situations it is preferred that the ratio of the size of a spot, to the size of the image of the cell on the array of detection elements is 1/1 or less, preferably less than 1/1 and higher than 1/100, more preferably less than 1/1 and higher than 1/40, more preferably less than 1/1 and higher than 1/10, more preferably less than 1/1 and higher than 1/4, more preferably less than 1/1 and higher than 1/2.

Thus, it is often preferred that the spatial representation exposed onto the array of detection elements is subject to such a linear enlargement that the ratio of the image of a linear dimension on the array of detection elements to the original linear dimension in the sample domain is smaller than 40:1, normally at the most 20:1, preferably smaller than 10:1 and in many cases even at the most 6:1 or even smaller than 4:1.

It is often preferred that the cells are imaged on at the most 25 detection elements, in particular on at the most 16 detection elements and more preferred at the most 9 detection elements, such as at the most 5 detection elements, or even on at the most 1 detection element. The larger number of elements per cell will provide more information on the individual cells, while the smaller number of elements per cell will increase the total count that can be made per exposure.

Statistics.

As mentioned above, the size of the volume is suitably adapted to the desired statistical quality of the determination. Thus, where the determination is the determination of the number of cells in a volume, or the determination of the size and/or shape of cells, the size of the volume of the liquid sample is preferably sufficiently large to allow identification therein of at least two of the cells. More preferably, the size of the volume of the liquid sample is sufficiently large to allow identification therein of at least four of the cells. This will correspond to a repeatability error of approximately 50%. Still more preferably, the size of the volume of the liquid sample is sufficiently large to allow identification therein of at least 10 of the cells. This will correspond to a repeatability error of approximately 33%. Even more preferably, the size of the volume of the liquid sample is sufficiently large to allow identification therein of at least 50 of the cells. This will correspond to a repeatability error of approximately 14%.

Evidently, where possible, it is preferred to aim at conditions where the size of the volume allows identification of even higher numbers. Thus, when the size of the volume of the liquid sample is sufficiently large to allow identification therein of at least 100 of the cells, it will correspond to a repeatability error of approximately 10%, and when the size of the volume of the liquid sample is sufficiently large to allow identification therein of at least 1000 of the cells, it will correspond to a repeatability error of as low as approximately 3%.

Stand Still.

In a preferred embodiment of the invention the cells being assessed are at stand still or substantially at stand-still during analysis, thus allowing the optimal use of measurement time in order to improve any signal to noise conditions. This arrangement also eliminates any error which could be inherent in the assessment of cells caused by variation in flow conditions, particularly when an assessment of a property is a volume related property such as the counting of cells in a volume of sample.

Flow System.

The introduction of cell and reagent material into the sample domain may be provided by means of a flow system. The flow system may provide at least one of several operations to be carried out on the samples, said operations being selected from but not limited to transport, mixing with reagent, homogenising of sample and optionally reagent, heat treatment, cooling, sound treatment, ultra sound treatment, light treatment and filtering.

The sample in the device can be flown by the means of a flow system, which can be driven by a pump or a pressurised gas, preferably air, or by causing a pressure difference such that the pressure on the exterior of the inlet is higher than the pressure within at least a part of the system thus forcing the sample to flow through the inlet or by propelling means. In many embodiments of the present invention the flow in said flow system is controlled by one or more valves which can adjust the flow speed of the sample, see for example the flow systems described in PCT/DK98/000175.

Detection Device.

The image which can be detected from the sample can for instance be detected by an array of detection elements, the array of detection elements comprising individual elements, each of which is capable of sensing signals from a part of the sample area, the array as a whole preferably being capable of sensing signals from substantially all of the sample area, or at least a well defined part of the sample area. The array of detection devices may for example be a one-dimensional array or a two-dimensional array. In order to facilitate the assessment of cells the intensities detected by the array of detection elements are processed in such a manner that representations of electromagnetic signals from the cells are identified as distinct from representations of electromagnetic background signals.

The detection means may comprise any detectors capable of sensing or detecting the signal emitted from the sample such as a fluorescence signal.

In a preferred embodiment detection means comprises a detector being an array of detecting devices or detection elements, such as a charge coupled device (CCD) the CCD may be a full frame CCD, frame transfer CCD, interline transfer CCD, line scan CCD, an eg. wavelength intensified CCD array, a focal plane array, a photodiode array or a photodetector array, such as a CMOS. The CMOS is preferably a CMOS image sensor with on-chip integrated signal condition and/or signal processing. Independent of the choice of any of the above detection devices the detection means may further comprise a white/black or colour CCD or CMOS.

Furthermore, the detection device may be included in a scanning microscope, such as a confocal scanning microscope.

Focusing—Lenses.

The inclusion of a focusing device for the focusing of a signal from the sample onto the detection elements in such a manner as to maximise the collection angle, the collection angle being defined as the full plane angle within which a signal is detected, has in many situations been found to give improved conditions for an assessment.

The collection angle of a focusing arrangement used can have effect on the intensity of any signal collected on the array of detection elements. When high sensitivity is needed it is therefore practical to increase the collection angle. The preferred size of the collection angle can also be determined by other requirements which are made to the system, such as focusing depth. In these situations the collection angle of the focusing means is preferably at least 2 degrees, preferably more than 5 degrees, more preferably more then 15 degrees, more preferably more than 20 degrees, more preferably more than 50 degrees, more preferably more than 120 degrees, more preferably more than 150 degrees.

Signal.

The signals measured from one or more detection elements may be corrected for systematic or varying bias by the use of a calculating means, the bias correction being accomplished by the use of one or more pre-defined value(s), preferably where each measured signal for one or more detection elements in said array of detection elements has one or more pre-defined value(s), more preferably where each pre-defined value is determined on the bases of one or more of any previous measurements.

The bias correction may be performed by subtracting the results obtained in one or several of other measurements from the measured signal, preferably where the other measurements are one or several of measurements of the same sample, or sample material, more preferably where the other measurement is the measurement taken previously of the same sample or sample material.

Processor.

Information of the signals detected by the detection means are input into a processor for processing, displaying and optionally storing the information.

The at least one quality or at least one quantity parameter of the cells is obtained by processing of the signals detected by the detection means. This processing can e.g. include conversion of the raw data using a pre-determined algorithm to obtain the quality or quantity parameter. The processing can also include use of a calibration curve or standard curve that specifies the relationship between the signal and the parameter of interest.

The signal information may be displayed on a display connected to the processor and/or printed. The information displayed may be any kind of information relating to the signals measured and/or the system used, such as a number, size distribution, morphology, classification of cells, excitation wavelength, emission wavelength, magnification. In particular the data processing means is capable of distinguishing partially overlapping areas of product.

DETAILED DESCRIPTION OF THE DRAWINGS

FIG. 1: 1A) Phase contrast image of proliferating Jurkat cells. 1B) The same cells as 1A were micrographed using a UV band pass filter cube, thereby showing the NAM (4) stained cells. 1C) The same cells as 1A were micrographed using a green long pass filter cube, thereby showing the PI stained cells. (20× magnification).

Figure 2:
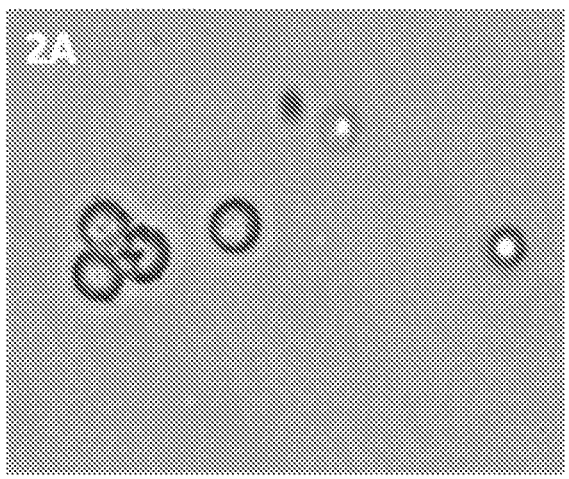
FIG. 2 shows phase contrast images and images from two filters of HEK293 cells that are stained with NAM and PI and discriminates between live and dead cells.
Figure 2:
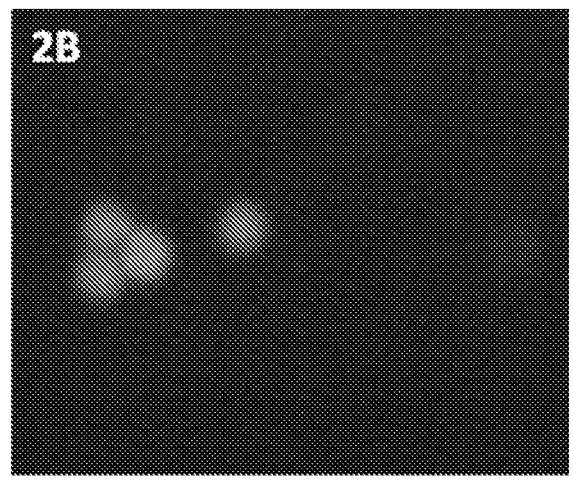
Figure 2:
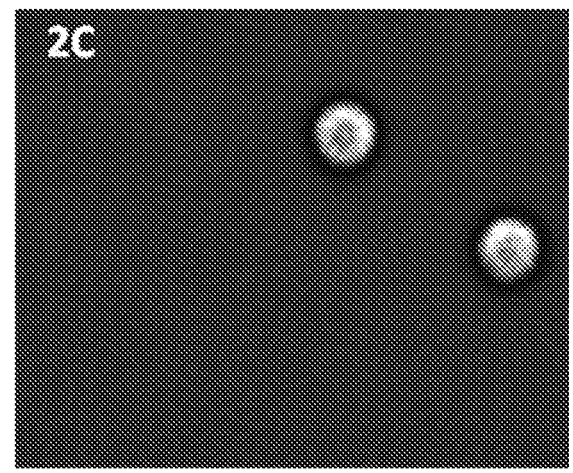

FIG. 2: 2A) Phase contrast image of HEK293 cells. 2B) The same cells as 2A were micrographed using a UV band pass filter cube, thereby showing the NAM stained cells. 2C) The same cells as 2A were micrographed using a green long pass filter cube, thereby showing the PI stained cells. (40× magnification).

Figure 3:
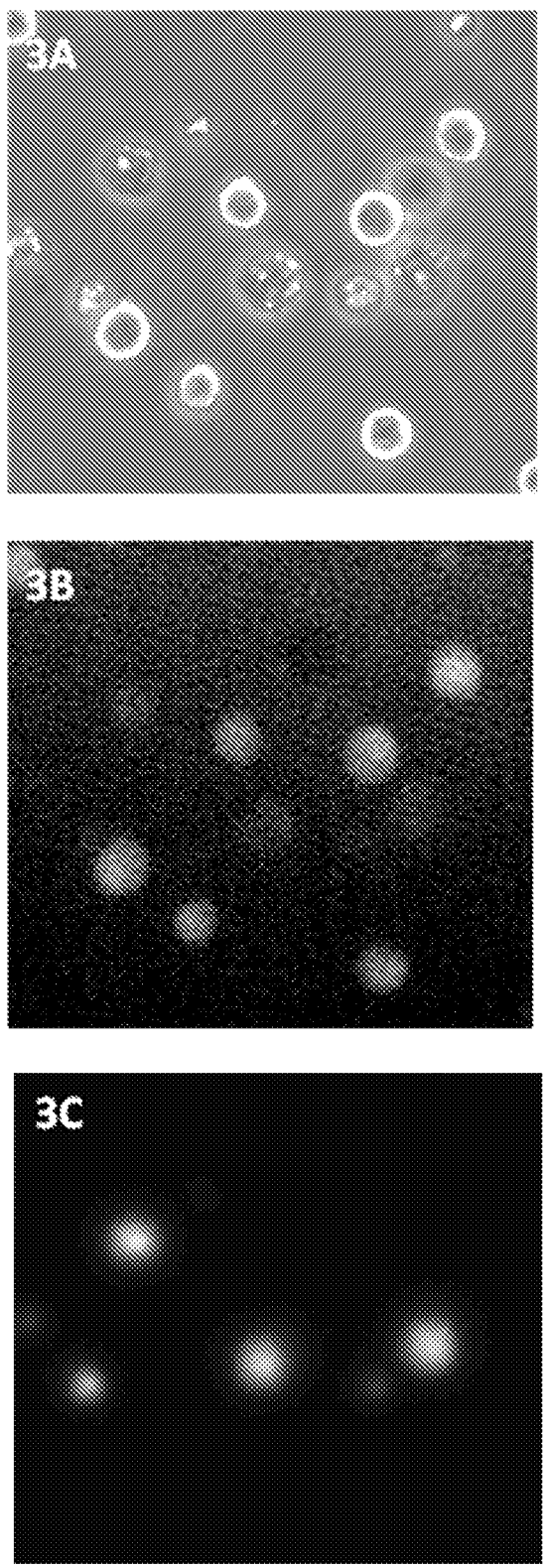
FIG. 3 shows phase contrast images and images from two filters of S2 cells that are stained with NAM and PI and discriminates between live and dead cells.

FIG. 3: 3A) Phase contrast image of S2 cells. 3B) The same cells as 3A were micrographed using a UV band pass filter cube, thereby showing the NAM stained cells. 3C) The same cells as 3A were micrographed using a green long pass filter cube, thereby showing the PI stained cells. (40× magnification).

Figure 4:
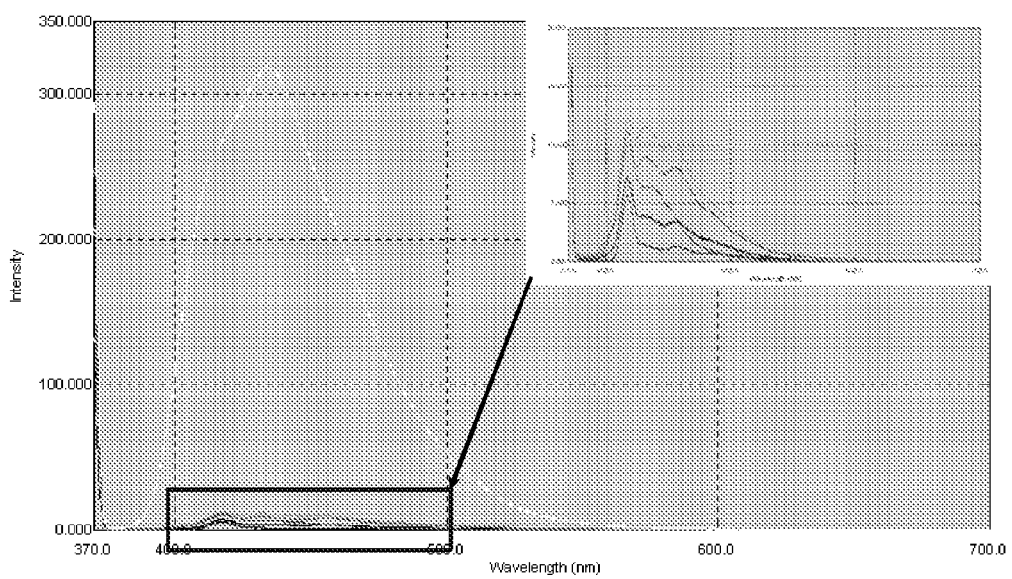
FIG. 4 shows excitation spectra of the reaction of NAM to both glutathione and oxidised glutathione.

FIG. 4: Excitation spectra. X axis; wavelength (nm), Y axis; relative intensity units. Black; water (background level), Blue; NAM, Red; reduced glutathione (GSH), Pink; oxidized glutathione (GSSG); Green; GSSG+NAM, yellow; NAM+GSH.

Figure 5:
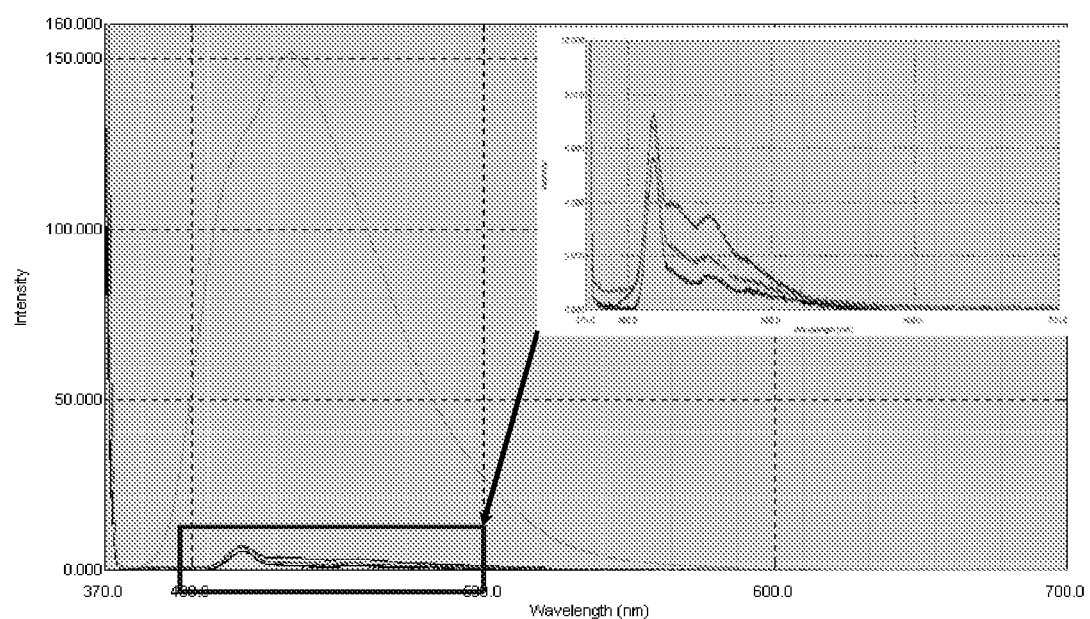
FIG. 5 shows excitation spectra of the reaction of NAM and DTT.

FIG. 5: Excitation spectra. X axis; wavelength (nm), Y axis; relative intensity units. Excitation spectra. X axis; wavelength (nm), Y axis; relative intensity units. Black; water (background level), Blue; NAM, Red; DTT, green; DTT+NAM.

Figure 6:
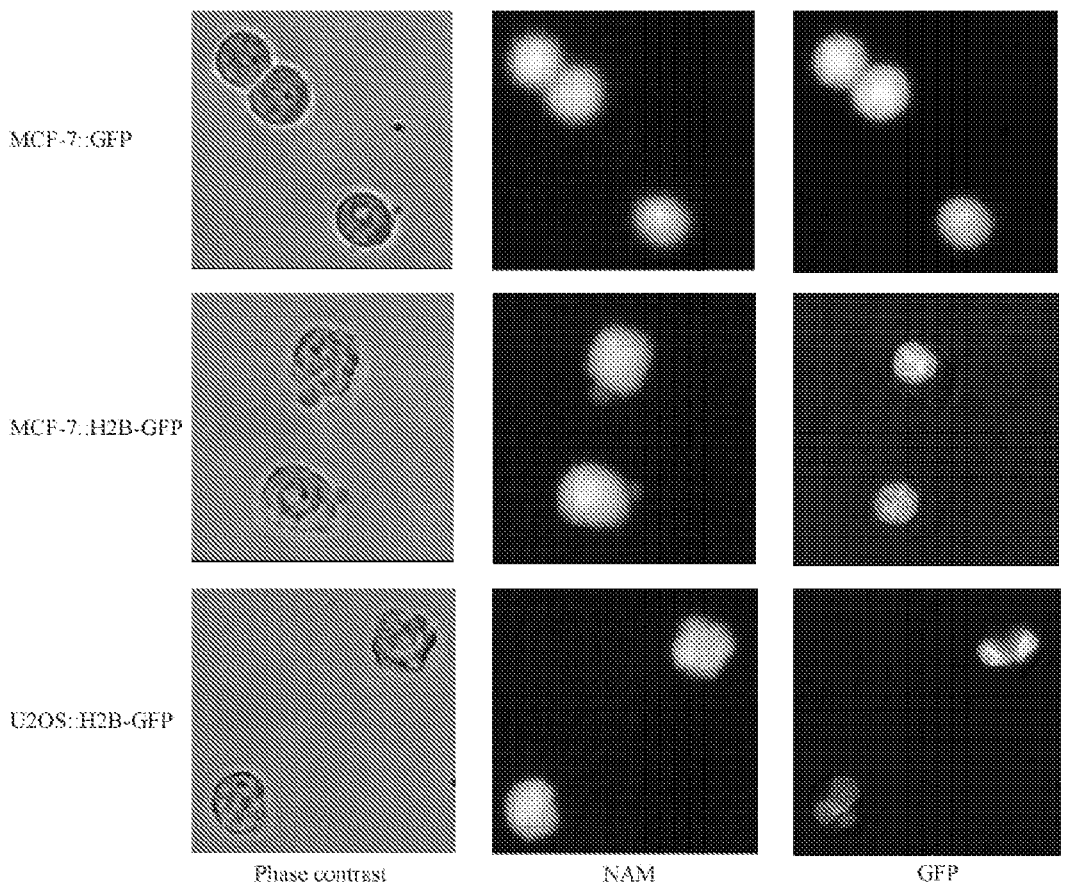
FIG. 6 shows fluorescent microscopy images and images from two filters of GFP-expressing MCF-7 and U2OS cells that are stained with NAM.

FIG. 6: Fluorescent microscopy of GFP-expressing MCF-7 and U2OS cells grown in T25 flasks. Cells were de-attached from the flasks prior to NAM staining and micrographing (40× magnification). Each panel shows the following images of the same cells: left; phase contrast, centre; NAM, right; GFP.

Figure 7:
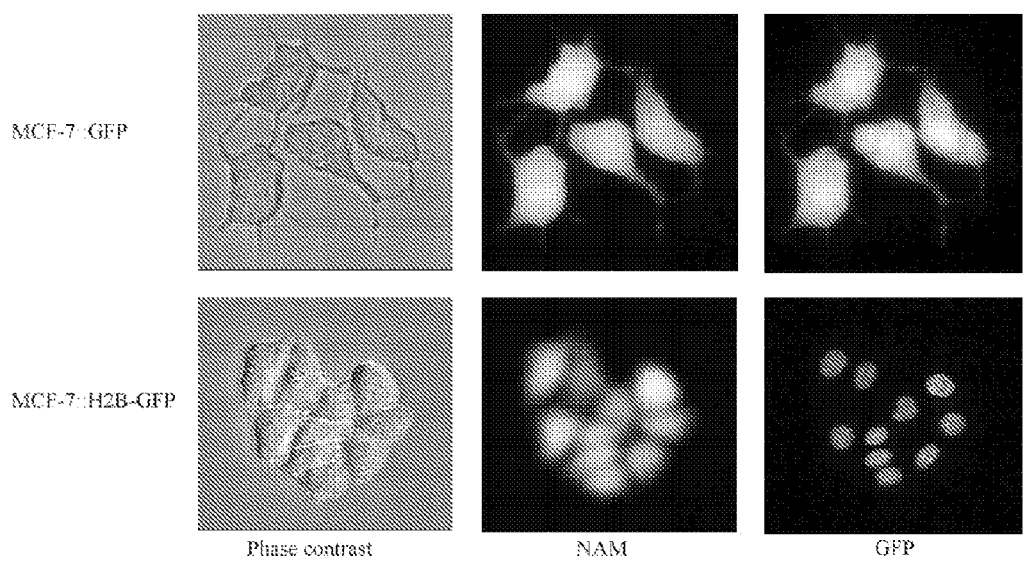
FIG. 7 shows fluorescent microscopy images and images from two filters of GFP-expressing MCF-7 cells that are stained with NAM.

FIG. 7: Fluorescent microscopy of GFP-expressing MCF-7 cells grown in chamber slides. Cells were NAM stained and micrographed (40× magnification). Each panel shows the following images of the same cells: left; phase contrast, centre; NAM, right; GFP.

Figure 8:
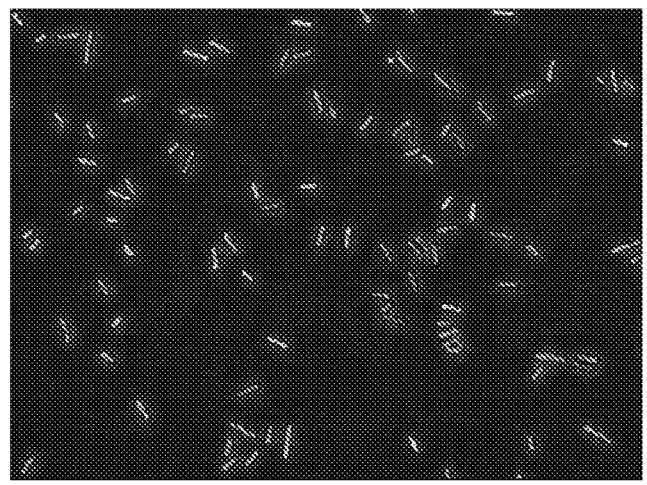
FIG. 8 shows phase contrast images and images from two filters of fission yeast cells stained with NAM and PI.
Figure 8:
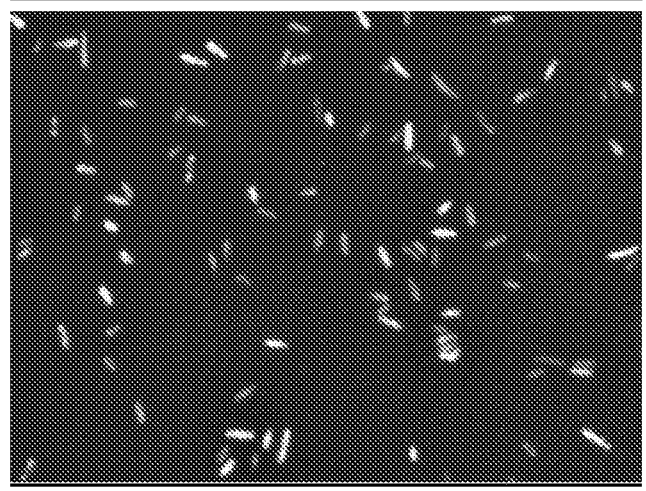
Figure 8:
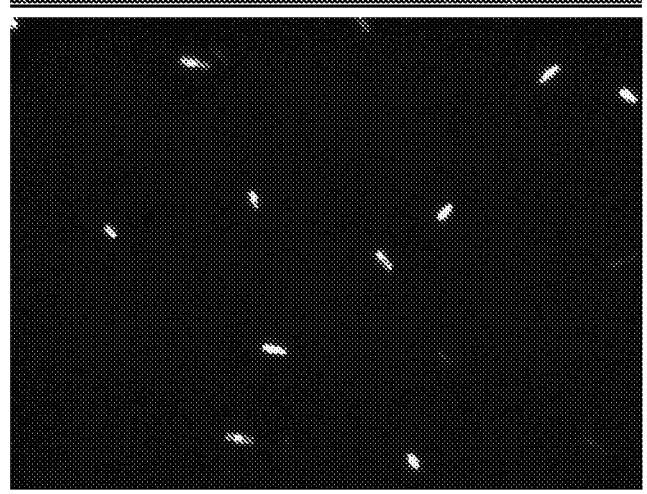

FIG. 8: Fluorescent microscopy of fission yeast cells (*Schizosaccharomyces pombe*) stained with NAM and propidium iodide and micrographed (20× magnification). Each panel shows the following images of the same cells: upper panel; phase contrast, middle panel; NAM, lower panel; propidium iodide (PI).

Figure 9:
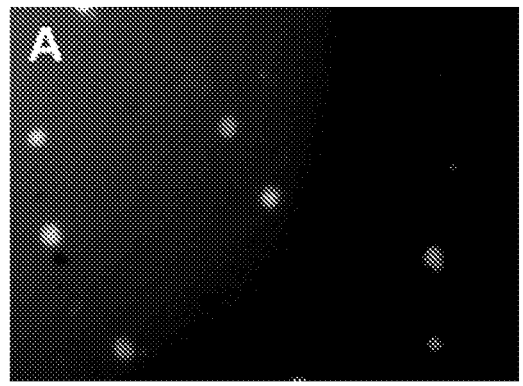
FIG. 9 shows phase contrast images and images from two filters of murine bone marrow cells stained with NAM and PI.
Figure 9:
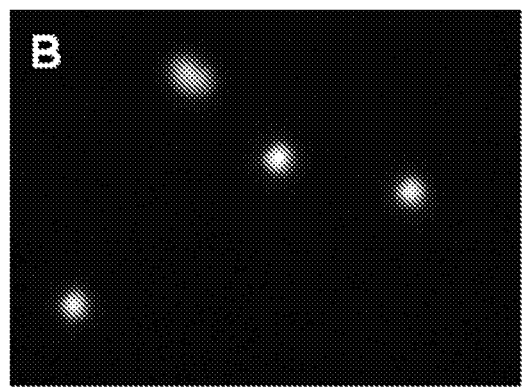
Figure 9:
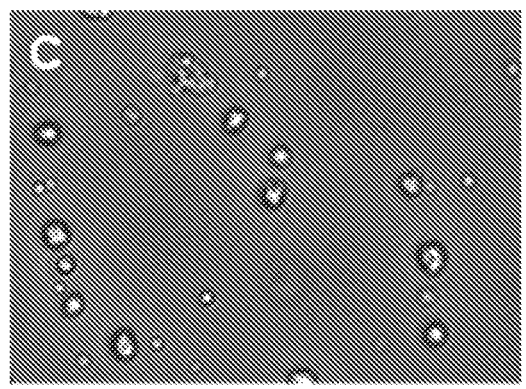

FIG. 9 A) Phase contrast image of primary murine splenocytes. B) The same cells as A) were micrographed using a UV band pass filter cube, thereby showing the NAM (4) stained cells. C) The same cells as A) were micrographed using a green long pass filter cube, thereby showing the PI stained cells (40× magnification).

Figure 10:
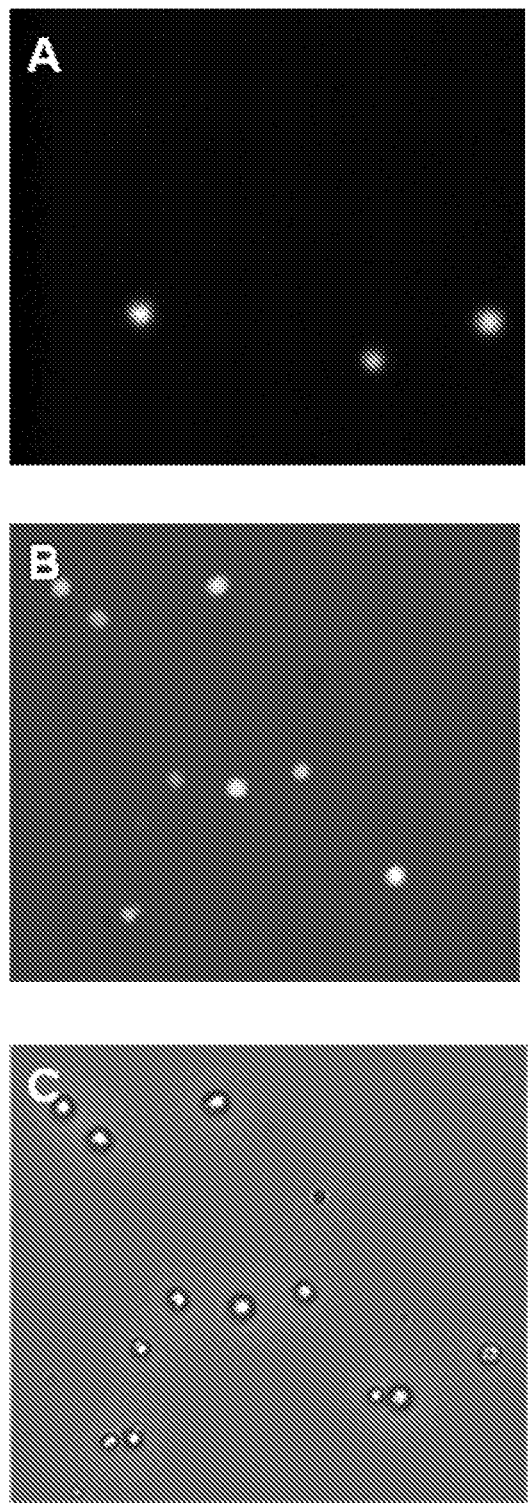
FIG. 10 shows phase contrast images and images from two filters of murine dendritic cells stained with NAM and PI.

FIG. 10: A) Phase contrast image of murine bonemarrow cells. B) The same cells as A) were micrographed using a UV band pass filter cube, thereby showing the NAM (4) stained cells. C) The same cells as A) were micrographed using a green long pass filter cube, thereby showing the PI stained cells (40× magnification).

Figure 11:
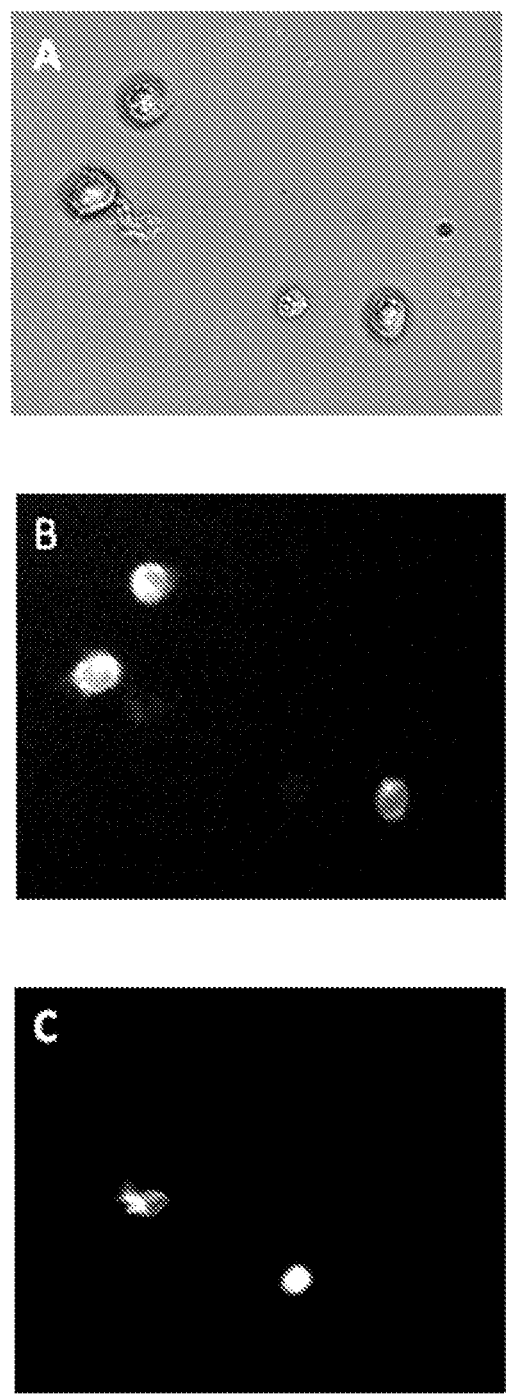
FIG. 11 shows phase contrast images and images from two filters of Jurkat cells that are stained with CPI and PI and discriminates between live and dead cells.

FIG. 11 CPI: A) Phase contrast image of proliferating Jurkat cells. B) The same cells as A) were micrographed using a UV band pass filter cube, thereby showing the CPI stained cells. C) The same cells as A were micrographed using a green long pass filter cube, thereby showing the PI stained cells. (20× magnification).

EXAMPLES RELATING TO NAM

Example 1

Use of NAM to Determine Viability of Proliferating Jurkat (JM) Cells (a T Lymphocyte Cell Line)

Materials and Methods.

Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 µL proliferating Jurkat cells (cell density $1.2 \times 10^6$, 99% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescent microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Results.

Observing the NAM stained cells in a fluorescent microscope under a UV filter it was clear that nearly all cells in the proliferating Jurkat cell culture were stained by NAM; only exception were PI positive cells (observed using the green long pass filter). (See 1A-1C in FIG. 1). Thus, PI and NAM seem to be complementary stains. As PI solely stains cells with disrupted plasma membrane (dead cells), this indicates that NAM stains cells with intact plasma membrane (live cells).

Example 2

Use of NAM to Determine Viability of HEK293 Cells (a Human Embryonic Kidney Cell Line)

Materials and Methods.

HEK293 cells were grown at 37° C. in a humidified air atmosphere with 5% $CO_2$ in DMEM (Invitrogen, #31966) supplemented with 10% heat-inactivated fetal bovine serum (Invitrogen, #10108-165). Cells were harvested with 0.5 mL of trypsin (Invitrogen, #25300) and neutralized with 5 mL medium (DMEM+10% FCS) two days after they had reached full confluency. These outgrown HEK293 cells (cell density $1.6 \times 10^6$, 78% viable determined using the NC-100 Nucleo-Counter system following the manufacturer's (ChemoMetec) protocol) were stained with 10 µg/mL NAM (Sigma, #01665). Another cell sample were treated with 0.25% Triton X-100 (Sigma, #T9284) and hereafter added 10 µg/mL NAM. After staining, each cell sample was loaded into a Nucleo-Cassette, containing the DNA stain propidium iodide (PI). The cells were investigated using an Olympus IX50 fluorescent microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Results.

As with the proliferating Jurkat cells, NAM and PI were found to complementary stain the outgrown HEK293 cells as revealed by fluorescence microscopy. (See 2A-2C in FIG. 2). Thus, NAM also functions to determine viability in stressed and outgrown cells. All Triton X-100 treated cells were PI positive and NAM negative, this suggests that an intact cell membrane is required for NAM staining.

Example 3

Use of NAM to Determine Viability of *Drosophila* S2 Cells (*Drosophila melanogaster* Schneider line-2 (S2) cells were originally derived from late embryonic stage *Drosophila* embryos.)

Materials and Methods.

*Drosophila* S2 cells were grown at 28° C. without shaking in Schneider's *Drosophila* medium (Invitrogen, #21720)

supplemented with 10% heat-inactivated fetal bovine serum (Invitrogen, #10108-165). S2 cells (cell density $1.7 \times 10^7$, 99% viable determined using the YC-100 NucleoCounter system with diploid settings following the manufacturer's (ChemoMetec) protocol) were diluted 10 times in PBS and stained with 10 µg/mL NAM (Sigma, #01665). Cells were loaded into a NucleoCassette, containing the DNA stain propidium iodide (PI). The cells were investigated using an Olympus IX50 fluorescent microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Results.

As with the proliferating Jurkat cells and the outgrown HEK293 cells, NAM and PI were found to complementary stain S2 cells as revealed by fluorescence microscopy. (See 3A-3C in FIG. 3). Hence, NAM can also be used to measure viability in insect cells.

Example 4

The Reaction of N-(9-acridinyl)maleimide (NAM) with —SH Reagents

Materials and Methods.

The excitation spectra of NAM, glutathione GSH, GSSG and DTT and combinations thereof were obtained using a spectrofluorophotometer (RF-5301 Fluorescence Spectrophotometer, Shimadzu). 10 µL NAM dissolved in DMSO (100 µg/mL) were added to 3 mL distilled water (resulting concentration of NAM; 0.33 µg/mL) in a quartz cuvette and the excitation spectrum was recorded. Likewise were the spectra of NAM (0.33 µg/mL) together with GSH (167 µg/mL), NAM (0.33 µg/mL) together with GSSG (167 µg/mL), NAM together with DTT (167 µg/mL), GSH (167 µg/mL) alone, GSSG (167 µg/mL) alone and DTT (167 µg/mL) alone recorded.

Results.

NAM, glutathione (GSH and GSSG) and DTT alone only exhibited very weak fluorescence, however, mixing NAM with DTT or GSH, but not GSSG, gave a strong synergistic effect with respect to fluorescence. See FIG. 4 and FIG. 5. As NAM together with glutathione GSH and DTT exhibit much stronger fluorescence than the additive effect, suggests that NAM reacts with glutathione (GSH) and DTT and forms a new fluorescent compound.

Example 5

Reduced NAM Localizes to the Cytosol and Nucleus

Materials and Methods.

MCF-7 (ATTC HTB-22) and U2OS (ATTC HTB-96) cells were cultivated in RPMI (Invitrogen, #61870)+10% FCS (Invitrogen, #10108-165). Cells were transfected with, respectively, pEGFP-C1 (Clontech) and pBOS-H2B-GFP (Pharmingen, BD Biosciences) using Lipofectamine 2000 (Invitrogen, #11668-027) according to manufacturer's instructions. Stable cells lines expressing GFP (green fluorescent protein) or H2B-GFP (GFP N-terminally fused to histone H2B) were cultivated in, respectively, T25 flasks and in chamber slides (Nunc) to 75% confluency. Cells from T25 flasks were harvested with 0.5 ml of trypsin (Invitrogen, #25300), neutralized with 5 ml of medium (RPMI+10% FCS), stained with 10 µg/ml NAM (N-(9-acridinyl), maleimide, Sigma, #01665) prior to mounting on a microscope slide. Cells grown on chamber slides were directly stained with 10 µg/ml NAM (N-(9-acridinyl)-maleimide). Olympus IX50 was used for microscopy, and images were captured using a Lumenera CCD camera and in-house developed software. GFP and NAM fluorescence were detected using, respectively, U-MNIB3 and U-MNUA2 filter cubes (Olympus).

Results.

Cells expression GFP or H2B-GFP were used for determining the intracellular localization of fluorescent NAM. GFP localizes to the cytosol and nucleus (Seibel, N. M., Eljouni, J, Nalaskowski, M. M., and Hampe, W. Anal Biochem. 2007, 368:95-9.), whereas the H2B-GFP fusion protein exclusively localizes to chromatin and, hence, in the nucleus (Kanda, T., Sullivan, K. F., and Geoffrey, M. W. Curr. Biology. 1998, 8:377-385).

Fluorescent microscopy of GFP-expressing cell lines revealed that NAM and GFP co-localize completely, implying that NAM is found in both the nucleus and cytosol (FIGS. 6 and 7, upper panels). Supporting this notion microscopy of H2B-GFP-expressing cells showed that NAM and H2B-GFP only partial co-localize. NAM is found outside as well as inside the nucleus (FIG. 6 middle panel and FIG. 7 lower panel).

Example 6

NAM Staining of Fission Yeast

Materials and Methods.

S. pombe strain Eg328, $h^{90}$ smt-0 ura4-D18, (ATCC 90720; Styrkarsdottir U et al. Curr. Genet. 23: 184-186, 1993) was grown in a rotary shaker at 29° C. to a density of $1 \times 10^7$ cells/ml in EMM minimal medium (Moreno et al., Methods Enzym. 194: 795-823, 1991) supplemented with 10 mM of L-uridine (Sigma, U3750). Cells were collected by centrifuging, washed with sterile water and stained with 10 µg/ml NAM (N-(9-acridinyl)-maleimide, Sigma, #01665) and 10 µg/ml propidium iodide (Applichem, #A2261.9010) prior to mounting on a microscope slide. Olympus IX50 was used for microscopy, and images were captured using a Lumenera CCD camera and in-house developed software. Propidium iodide and NAM fluorescence were detected using, respectively, U-MWG2 and U-MNUA2 filter cubes (Olympus).

Results.

NAM specifically stains living mammalian and insect cells (example X and Y), probably by reacting with reduced peptide thiols. In order to evaluate whether NAM can be used for discriminating between living and dead yeast cells S. pombe cells were stained with propidium iodide (PI) and NAM. Fluorescent microscopy revealed that NAM stains both living and dead yeast cells (FIG. 8). This is quite surprising since the amount of reduced peptide thiols, similar to other eukaryotes, is low in dead yeast cells (Østergaard, H, Tachibana, C., and J. R. Winther, J. Cell Biol. 2004. 166(3):337-45). This indicates that NAM, in yeast cells, reacts with additionally cellular components. It has been reported that upon reaction with sulfite NAM fluoresces strongly (Akasaka, K., Matsuda, H., Ohrui, H., Meguro, H., and Suzuki, T. Agric. Biol. Chem. 54: 510-504, 1990). Since yeast cells has the ability to accumulate sulfite (Hansen, J and Kielland-Brandt, M. C. Nature Biotech. 14: 1587-1591, 1996) the NAM staining of dead yeast cells may be explained by accumulation of sulfite in these cells. Similar to mammalian cells NAM apparently localizes to both the nucleus and cytosol and is not a DNA specific stain (FIG. 8).

Example 7

Use of NAM to Determine Viability of Primary Murine Splenocytes

Materials and Methods.

The spleen from a C57BL/6 mouse was placed in ice-cold PBS and gently ground using the end of a sterile syringe. The suspension was centrifuged at 300 g for 10 minutes; the pellet was resuspended in 1 mL 0.83% $NH_4Cl$ to lyse erythrocytes and incubated for 3 minutes on ice. The cells were then added 14 mL PBS and centrifuged at 300 g for 10 minutes. The splenocytes were resuspended in RPMI (Invitrogen, #61870) supplemented with 10% heat-inactivated fetal bovine serum (Invitrogen, #10108-165), 100 U/mL penicillin and 100 µg/mL streptomycin (Invitrogen, #15140-122). The cell clumps were allowed to sediment and were removed by pipetting, and the resulting single cell suspension was used. 90 µL splenocytes (cell density $1.7 \times 10^6$, 90% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescence microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Results.

Observing the NAM stained cells under a fluorescence microscope using a UV filter it was clear that nearly all the primary spleen cells were stained by NAM; only exception were PI positive cells (observed using the green long pass filter). (See A-C in FIG. 9). Thus, NAM also functions to determine viability in murine primary splenocytes.

Example 8

Use of NAM to Determine Viability of Bone Marrow Derived Cells

Materials and Methods.

The bone marrow cells were harvested aseptically in the laminar flow hood. Briefly, bilateral tibia and femur were aseptically removed, freed of surrounding soft tissue, and placed in a petri dish with 10 mL 70% ethanol. After 2 minutes they were transferred to ice cold PBS. The bone marrow cavity was then flushed with 5 ml cold PBS using a 5-ml syringe with a 27-gauge needle attached, and the cells were collected from each bone. The cells were centrifuged at 300 g for 10 min, the supernatant was discarded, and cells were washed twice. After the second wash the cell pellet was resuspended in RPMI 1640 (Invitrogen, #61870) supplemented with 10% heat-inactivated fetal bovine serum (Invitrogen, #10108-165), 100 U/mL penicillin and 100 µg/mL streptomycin (Invitrogen, #15140-122). 90 µL bone marrow cells (cell density $1.7 \times 10^6$, 93% viable determined using the NC-100 NucleoCounter system following the manufacturer's (ChemoMetec A/S) protocol) were added 10 µL NAM (N-(9-acridinyl)maleimide, Sigma, #01665, CAS no. 49759-20-8) dissolved in DMSO (100 µg NAM pr. mL DMSO) and mixed by pipetting. Cells were loaded into a NucleoCassette, containing the DNA stain propidium iodide (PI). The cells were investigated using an Olympus IX50 fluorescent microscope, and images were captured using a Lumenera CCD camera and in-house developed software. PI and NAM fluorescence were detected using, respectively, U-MWG2 (green long pass: 510-550 nm) and U-MNUA2 (UV band pass, 330-385 nm) filter cubes (Olympus).

Results.

Observing the NAM stained cells under a fluorescent microscope using a UV filter it was clear that nearly all the primary bone marrow cells were stained by NAM; again only exception were PI positive cells (observed using the green long pass filter). (See A-C in FIG. 10). Thus, NAM can also be used for to determining viability of bone marrow cells which consist of a mixture of various cell types such as fibroblasts, odioblasts, macrophages and stem cells.

Examples Relating to CPI

Example 9

Application of 7-diethylamino-3-((4'-(iodoacetyl)amino)phenyl)-4-methylcoumarin (CPI) as Marker of Cell Viability Materials and Methods.

Jurkat (JM) cells were grown at 37° C. in a humidified air atmosphere with 5% $CO_2$ in RPMI (Invitrogen, #61870) supplemented with 10% heat-inactivated fetal bovine serum (Invitrogen, #10108-165). 90 µL proliferating Jurkat cells (cell density $1.1 \times 10^6$, 98% viable determined using the NC-100 NucleoCounter system following the manufacturer's (ChemoMetec) protocol) were added 10 µL CPI (7-diethylamino-3-((4'-(iodoacetyl)amino)phenyl)-4-methylcoumarin, Sigma 78264 CAS no. 76877-34-4) dissolved in DMSO (100 µg CPI pr. mL DMSO) and mixed by pipetting. Cells were loaded into a NucleoCassette, containing the DNA stain propidium iodide (PI). The cells were investigated using an Olympus IX50 fluorescent microscope, and images were captured using a Lumenera CCD camera and in-house developed software. PI and CPI fluorescence were detected using, respectively, U-MWG2 (green long pass: 510-550 nm) and U-MNUA2 (UV band pass, 330-385 nm) filter cubes (Olympus).

Results.

Observing the CPI stained cells under a fluorescent microscope using a UV filter it was clear that nearly all cells were stained by CPI; and (as with the maleimides NAM, CPM and PM) only exception were PI positive cells (observed using the green long pass filter). (See A-C in FIG. 11).

The invention claimed is:

1. A method for quantitative and/or qualitative assessment of cells, said method comprising: providing a sample comprising cells for which viability should be determined, adding a labeling agent to said sample, wherein said labeling agent comprises 7-diethylamino-3-((4'-(iodoacetyl)amino)phenyl)-4-methylcoumarin (CPI), reacting said labeling agent with said sample to label viable cells so as to obtain a labeled sample, quantitatively and/or qualitatively assessing the viability of the cells in the labeled sample.

2. The method according to claim 1, wherein the step of assessing the viability of said cells comprises assessing one or more parameter selected from the group consisting of: cell division, proliferation, apoptosis, or necrosis wherein the method includes the optional step of determining one or more of: mobility, spatial orientation or morphology of said cells.

3. The method according to claim 1, wherein the step of assessing cell viability includes quantification of viable cells.

4. The method according to claim 1, wherein the biological sample is selected from a body fluid sample, a tissue sample, a fermentation sample, a liquid cultivation sample, a cell culture sample, a water sample, a beverage sample, a pharmaceutical sample or a microelectronic product.

5. The method according to claim 1, wherein the sample is a biological sample selected from a blood sample, a urine sample, a saliva sample, a semen sample, a solubilized tissue sample or a milk sample.

6. The method according to claim 1, wherein the sample is a biological sample selected from a liver sample, a kidney sample, a muscle sample, a brain sample or a lung sample.

7. The method according to claim 1, wherein the sample is a biological sample selected from a human sample, a mouse sample, a rat sample, a monkey sample, and a dog sample.

8. The method according to claim 1, wherein the sample is a biological material selected from a bacterial culture, a yeast culture, a mammalian cell culture, or a protozoa culture.

9. The method according to claim 1, wherein the sample is exposed to light before assessment.

10. The method according to claim 9, wherein the light is of any wavelength between 200 nm to 1700 nm.

11. The method according to claim 1, wherein the sample emits light after excitation from an external light source for assessment.

12. The method according to claim 11, wherein the emitted light from the sample is of any wavelength between 300 nm to 800 nm.

13. The method according to claim 9, wherein the light is focused by a focusing system, comprising one or more lenses, or mirrors.

14. The method according to claim 9, wherein the light originates from a light source selected from the group consisting of: a thermal light source, a halogen lamp, a gas lamp, a xenon lamp, a light emitting diode (LED), a laser or a laser diode.

15. The method according to claim 9, wherein the light can originate from one, two or more light sources.

16. The method according to claim 1, wherein the biological sample is, upon detection, magnified to such extent whereas the ratio between image and sample is smaller than 10:1.

17. The method according to claim 1, wherein determination of cell viability includes determination of development, germination and/or reproduction.

18. The method according to claim 1, including a double labeling step wherein a dead cell labeling agent is also added to the sample.

\* \* \* \* \*

UNITED STATES PATENT AND TRADEMARK OFFICE
CERTIFICATE OF CORRECTION

PATENT NO.         : 8,697,390 B2                                   Page 1 of 1
APPLICATION NO.    : 13/003982
DATED              : April 15, 2014
INVENTOR(S)        : Mette Elena Skinderso et al.

It is certified that error appears in the above-identified patent and that said Letters Patent is hereby corrected as shown below:

In the Claims

Column 19, line 1, claim 4 – please delete "biological".

Signed and Sealed this
Eighth Day of July, 2014

Michelle K. Lee
*Deputy Director of the United States Patent and Trademark Office*